United States Patent [19]

Tahara et al.

[11] Patent Number: 4,581,355

[45] Date of Patent: * Apr. 8, 1986

[54] 3-INDOLECARBOXAMIDES FOR CONTROL OF CIRCULATORY DISEASES

[75] Inventors: Tetsuya Tahara; Tsuguo Ikebe; Yutaka Maruyama, all of Oita; Osamu Yaoka, Fukuoka; Yohji Miura, Saitama, all of Japan

[73] Assignee: Yoshitomi Pharmaceutical Industries, Ltd., Osaka, Japan

[*] Notice: The portion of the term of this patent subsequent to Mar. 18, 2003 has been disclaimed.

[21] Appl. No.: 680,727

[22] Filed: Dec. 12, 1984

[30] Foreign Application Priority Data

Dec. 28, 1983 [JP] Japan ................. 58-251149

[51] Int. Cl.$^4$ .................... A61K 31/55; C07D 401/12
[52] U.S. Cl. .................. 514/212; 260/245.7; 514/323; 514/414; 546/201; 546/223; 548/467
[58] Field of Search ............... 546/201; 548/492, 465, 548/467; 260/245.7; 514/414, 323, 212

[56] References Cited

U.S. PATENT DOCUMENTS

| | | | |
|---|---|---|---|
| 2,814,625 | 11/1957 | Specter et al. | 546/201 |
| 3,527,761 | 9/1970 | Archibald et al. | 546/201 |
| 3,869,463 | 3/1975 | Archibald | 546/201 |
| 4,064,255 | 12/1977 | Champselx et al. | 546/201 |
| 4,140,691 | 2/1979 | Weston et al. | 546/201 |

FOREIGN PATENT DOCUMENTS

| | | | |
|---|---|---|---|
| 2407465 | 2/1973 | Fed. Rep. of Germany | 546/201 |
| 2708913 | 9/1977 | Fed. Rep. of Germany | 546/201 |
| 1255928 | 11/1961 | France | 546/201 |
| 1345872 | 2/1974 | United Kingdom | 546/201 |

OTHER PUBLICATIONS

March, *Advanced Organic Chemistry*, 1st ed., McGraw-Hill, 1968, p. 336.
Archibald, J., et al., Journal of Medicinal Chemistry, vol. 14, pp. 1054–1059, (1971).

*Primary Examiner*—Richard A. Schwartz
*Attorney, Agent, or Firm*—Sughrue, Mion, Zinn, Macpeak and Seas

[57] ABSTRACT

3-Indolecarboxamide compounds of the formula:

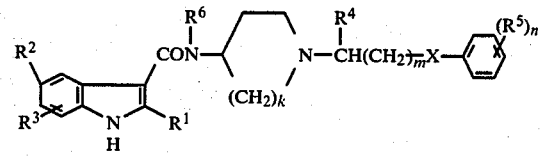

inclusive of pharmaceutically acceptable acid addition salt and/or hydrate forms thereof, wherein $R^1$ is hydrogen or $C_{1-4}$ alkyl; each of $R^2$ and $R^3$ is hydrogen, halogen, $C_{1-4}$ alkyl, $C_{1-4}$ alkoxy, benzyloxy, $C_{2-6}$ alkanoyloxy or hydroxy; $R^4$ is hydrogen or $C_{1-4}$ alkyl; $R^5$ is hydrogen, halogen, $C_{1-4}$ alkyl, $C_{1-4}$ alkoxy or hydroxy; $R^6$ is hydrogen or $C_{1-4}$ alkyl; X is oxygen, sulfur or direct bond; each of k and m is an integer of 1 to 3; and n is 1 or 2, are useful as drug for the prevention and treatment of various circulatory diseases.

12 Claims, No Drawings

3-INDOLECARBOXAMIDES FOR CONTROL OF CIRCULATORY DISEASES

FIELD OF THE INVENTION

The present invention relates to novel and therapeutically valuable 3-indolecarboxamide compounds, pharmaceutically acceptable acid addition salts thereof and hydrates thereof, methods for preparing the 3-indolecarboxamide compounds and pharmaceutical compositions containing at least one 3-indolecarboxamide compound.

DESCRIPTION OF THE PRIOR ART

It is well known that leukotrienes (hereinafter referred to as LTs) are formed by 5-lipoxygenase in the metabolic pathway of arachidonic acid apart from the formation of prostaglandins by cyclooxygenase. Recently, the actions of LTs on hemodynamics attract much attention (Piper et al, Trends in Pharmacological Sciences, 75–77, 1983). In particular, LTs exhibit strong vasoconstrictive activity, by which the coronary blood flow is decreased by 50–70%. LTs formed by various stimuli induce vasospasm, ischemia, hypertension and so on. LTB (leukotriene B) may cause atherosclerosis attack since biosynthesis of thromboxane $A_2$ ($TXA_2$) is accelerated by formation of LTB, and platelet aggregation is induced. Therefore, the compounds having 5-lipoxygenase-inhibiting activity antagonize various etiological factors of some kind of diseases, and are especially useful as drugs for the prevention and treatment of various circulatory diseases.

U.S. Pat. No. 3,527,761 or Journal of Medicinal Chemistry, vol. 14, p. 1054 (1971) describes that the 3-indoleethylamine compounds including 3-[2-(4-(3-indolecarboxamido)1-piperidyl)ethyl]indole possess mainly antihypertensive activity, and in particular, indoramin (INN, 3-[2-(4-benzamido-1-piperidyl)ethyl]indole) is known as the compound having stronger antihypertensive activity among them. These compounds, however, do not exhibit 5-lipoxygenase-inhibiting activity, in practice.

SUMMARY OF THE INVENTION

As a result of various investigations, the present inventors have found that novel 3-indolecarboxamide compounds, pharmaceutically acceptable acid addition salts thereof and hydrates thereof exhibit 5-lipoxygenase-inhibiting activity and also vasodilating activity, hypotensive activity and cardiotonic activity (possitive inotropic activity), and are useful as drugs for the prevention and treatment of the various circulatory diseases such as hypertension, cardiac failure, angina pectoris, cerebral circulatory diseases.

DETAILED DESCRIPTION OF THE INVENTION

The 3-indolecarboxamide compounds of the present invention are represented by the following formula:

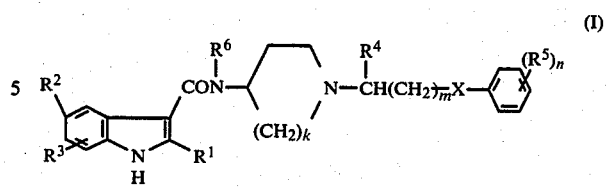

wherein $R^1$ is a hydrogen atom or a $C_{1-4}$ alkyl group; each of $R^2$ and $R^3$ is a hydrogen atom, a halogen atom, a $C_{1-4}$ alkyl group, a $C_{1-4}$ alkoxy group, a benzyloxy group, a $C_{2-6}$ alkanoyloxy group or a hydroxyl group; $R^4$ is a hydrogen atom or $C_{1-4}$ alkyl group; $R^5$ is a hydrogen atom, a halogen atom, a $C_{1-4}$ alkyl group, a $C_{1-4}$ alkoxy group or a hydroxyl group; $R^6$ is a hydrogen atom or a $C_{1-4}$ alkyl group; X is an oxygen atom, a sulfur atom or a direct bond; each of k and m is an integer of 1 to 3; and n is 1 or 2.

In the above definitions, $C_{1-4}$ alkyl group means methyl, ethyl, propyl, isopropyl, butyl or tertiary butyl; a halogen atom means fluorine, chlorine, bromine or iodine; a $C_{1-4}$ alkoxy group means methoxy, ethoxy, propoxy or butoxy; and a $C_{2-6}$ alkanoyloxy group means acetoxy, propinoyloxy, butyryloxy or pivaloyloxy.

More preferable compounds of the present invention are compounds of the formula (I) wherein $R^1$ is a hydrogen atom or a $C_{1-4}$ alkyl group; $R^2$ is a hydrogen atom, a halogen atom or a $C_{1-4}$ alkoxy group or a hydroxyl group; $R^3$ is a hydrogen atom, a halogen atom or a $C_{1-4}$ alkyl group; $R^4$ is a hydrogen atom or a $C_{1-4}$ alkyl group; $R^5$ is a hydrogen atom, a halogen atom, a $C_{1-4}$ alkoxy group or a hydroxyl group on the 4-position of the benzene ring; $R^6$ is a hydrogen atom; X is a direct bond; k is 2; m is 1 or 2; and n is 1.

Most preferable compounds of the present invention are compounds of the formula (I) wherein $R^1$ is a hydrogen atom or a $C_{1-4}$ alkyl group; $R^2$ is a hydroxyl group; $R^3$ is a hydrogen atom, a halogen atom or a $C_{1-4}$ alkyl group; $R^4$ is a hydrogen atom or a $C_{1-4}$ alkyl group; $R^5$ is a hydrogen atom, a halogen atom, a $C_{1-4}$ alkoxy group or a hydroxyl group on the 4-position of the benzene ring; $R^6$ is a hydrogen atom; X is a direct bond; k is 2; m is 1 or 2; and n is 1.

The compounds of formula (I) can be, for example, prepared by allowing a compound of the formula:

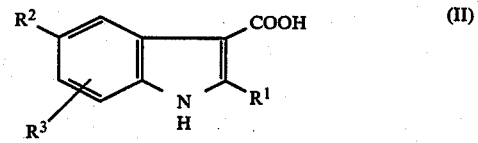

wherein each symbol is as defined above, or a functional derivative thereof to react with a compound of the formula:

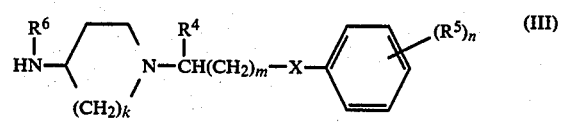

wherein each symbol is as defined above.

The reaction is carried out by a conventional amide preparation method or a peptide-synthesis method.

In case the compound of formula (II) is carboxylic acids, for example, the reaction is carried out in an inert solvent under cooling or heating in the presence of a condensing agent such as a carbodiimide (e.g. dicyclohexylcarbodiimide), titanium tetrachloride, a phosphorus halide (e.g. phosphorus trichloride or phosphorus oxychloride), diphenylphosphoryl azide or a quaternary pyridinium salt (e.g. 2-chloro-N-methylpyridinium iodide or 3-methanesulfonyloxy-N-methylpyridinium iodide).

When an acid halide (e.g. an acid chloride or an acid bromide) or a mixed acid anhydride (e.g. a mixed acid anhydride with a carbonic acid half lower alkyl ester, a lower alkanoic acid or a mixed acid anhydride with a lower alkylphosphoric acid) is used as the functional derivative of the carboxylic acids of formula (II), the reaction is carried out in an inert solvent at room temperature, or under cooling or heating, preferably in the presence of a deacidifying agent such as an organic base (e.g. triethylamine or pyridine) or an inorganic base (e.g. sodium hydrogencarbonate, an alkali carbonate or an alkali hydroxide).

In case a lower alkyl ester or an active ester (e.g. p-nitrophenyl ester, p-nitrobenzyl ester of p-chlorophenyl ester) is used as other functional derivative, the reaction is carried out in an inert solvent at room temperature or under refluxing, if desired, in the presence of a strong basic catalyst like sodium alkoxide.

The compounds of formula (II) wherein at least one of $R^2$ or $R^3$ is a hydroxyl group may be used by means of the protection of the hydroxyl group with a lower alkoxy group, a benzyloxy group, a lower alkanoyloxy group, a benzoyloxy group or a dihydropyranyloxy group for acylation of the compounds of formula (III) as mentioned above. And then the protecting group of the resulting compounds can be removed by treating with an acid or alkali or subjecting to catalytic hydrogenation on palladium carbon or platinum oxide and so on, if desired.

Further, the compounds of formula (I) can be prepared by allowing a compound of the formula:

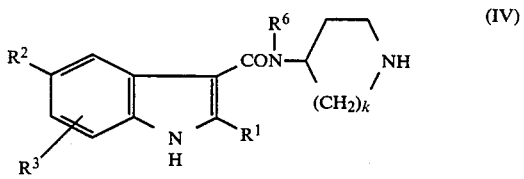
(IV)

wherein each symbol is as defined above, to react with a compound of the formula:

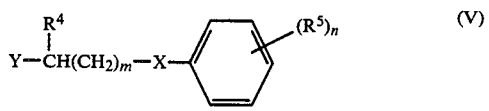
(V)

wherein Y is a halogen atom (e.g. chlorine, bromine or iodine), a lower alkylsulfonyloxy group (e.g. methanesulfonyloxy or ethanesulfonyloxy) or an arenesulfonyloxy group (e.g. p-toluenesulfonyloxy or benzenesulfonyloxy) and other symbols are as defined above, in an inert solvent at room temperature or under cooling or heating, preferably in the presence of a deacidifying agent such as sodium hydrogencarbonate, an alkali carbonate or an alkali hydroxide.

Any inert solvent can be used in practicing the above reaction, and preferably water, a lower alkanol (e.g. methanol ethanol, or isopropanol), an ester (e.g. ethyl acetate), an aromatic hydrocarbon (e.g. benzene or toluene), a halogenated hydrocarbon (e.g. methylene chloride or chloroform), a ketone (e.g. acetone or methyl ethyl ketone), an ether (e.g. diethyl ether, tetrahydrofuran or dioxane), dimethylformamide or dimethyl sulfoxide, or a mixutre thereof are used.

The compounds of the present invention are prepared as a racemate by using the starting compounds of formulae (III) and (V) having a chiral carbon atom. The present invention also embraces individual optically active isomers. The optically active compounds of formula (I) can, if desired, be prepared by resolving the resulting racemate in a conventional manner with an optically acitve acid (e.g. tartaric acid, dibenzoyltartaric acid, mandelic acid or 10-camphorsulfonic acid) or by using the optically active compounds of formulae (III) and (V) previously prepared as a starting compound.

The compounds of the present invention can, if desired, be converted into pharmaceutically acceptable acid addition salts thereof in a conventional manner by treating with an inorganic acid (e.g. hydrochloric acid, hydrobromic acid, phosphoric acid, nitric acid or sulfuric acid) or an organic acid (e.g. p-toluenesulfonic acid, methanesulfonic acid, citric acid, butyric acid, maleic acid, fumaric acid or tartaric acid).

The compounds of formula (I), pharmaceutically acceptable acid addition salts thereof and hydrates thereof exhibit 5-lipoxygenase-inhibiting activity and vasodilating, antihypertensive and cardiotonic activities with antihistaminic, antiserotonergic and adrenolytic activities, and are useful as drugs for the prevention and treatment of various circulatory diseases.

The compounds of the present invention showed 50% inhibitory concentration on 5-lipoxygenase of 0.1–100 μM. According to the pharmacological experiment conducted by the method of Yoshimoto et al. which is described in Biochem. Biophys. Res. Commum., vol. 107, p. 779–784 (1982), the compounds of Examples 2 and 3 showed strong 50% inhibitory concentration on 5-lipoxygenase of 0.44 μM and 0.18 μM, respectively.

The compounds of the present invention showed hypotensive activity at an oral dose of 0.1–30 mg/kg in spontaneous hypertensive rats and were 3 to 10 times or more as strong as indoramin mentioned previously.

The experiment on cardiotonic activity of the compounds of the present invention was conducted as follows: Dogs were anesthetized with sodium pentobarbital and heparin was administered intraveneously. The left venticular pressure and its max dP/dt were measured. Test compounds were injected at a volume of 10 to 30 μl into a catheter inserted into left coronary artery. The effects of test compounds on max dP/dt were shown as $ED_{30}$, a dose required to increase max dP/dt by 30% of the effects of 0.1 μg is isoproterenol. The $ED_{30}$ values of the compounds of Example 3 and 35 were 50 μg and 36 μg, respectively, and were superior to that of ouabain, cardiotonic glycoside with $ED_{30}$ of 60 μg.

Further, the compounds of the present invention are characteristic of very long-lasting activities.

The compounds of the present invention had a high vasoselectivity and characteristically very weak inhibitory activity in the central nervous system which often caused drowsiness or sedation and so on and very low acute toxicity. When sedative activity was observed by electroencephalograms in rabbits, indoramin showed a trend toward slow wave from the intraperitoneal dose of 3 mg/kg, but any changes on electroencephalograms of the compounds of the present invention were not observed even at the intraperitoneal dose of 100 mg/kg. The acute toxicity of the compounds of the present invention was studied in 5 male mice weighing 30 to 45 g. The mice were observed for 5 days after the oral administration of the test compound, and the mortality was calculated. All animals survived even at the dose of 1000 mg/kg of compound of Example 2, while all mice died at a dose of 500 mg/kg of indoramin.

The compounds of the present invention can be used as drugs for the prevention and treatment of various circulatory diseases in the form of a pharmaceutical composition with a suitable and conventional carrier like an excipient, an extender, a diluent or a solubilizer without harmful side effects to the patients.

The pharmaceutical composition can take the presentation form of tablets, granules, powder, capsules or injectable solution. The choice of carrier is determined by the preferred form of administration, the solubility of the compound and standard pharmaceutical practice.

FORMULATION EXAMPLE

Tablets containing 5 mg of compound of the present invention can be prepared on the following composition:

| | |
|---|---|
| Compound 2 (as hydrochloride) | 5.0 mg |
| Corn starch | 15.0 |
| Lactose | 60.0 |
| Microcrystalline cellulose | 16.0 |
| Talc | 3.0 |
| Magnesium stearate | 1.0 |
| | 100.0 mg |

The single dose of the compounds of the present invention in human adults usually ranges from 0.01 to 10 mg/kg depending on body weight, but it may vary depending upon the age, body weight, and/or severity of the condition to be treated as well as the response to the medication.

The present invention will be better understood from the following examples, but they are not to be construed as limiting the present invention.

EXAMPLE 1

A solution of 4.0 g of 5-fluoro-2-methylindole-3-carboxylic acid and 4.2 g of 4-amino-1-(2-phenylethyl)-piperidine in 80 ml of tetrahydrofuran was allowed to stand for a while to precipitate a salt. To the suspension was added 4.7 g of dicyclohexylcarbodiimide and the mixture was stirred under reflux for 3 hours. After cooling, the precipitated dicyclohexylurea was filtered off and the filtrate was concentrated. The residue was crystallized by treatment of hexane. The crystals were filtered with suction and recrystallized from ethyl acetate to yield 3.7 g of 5-fluoro-2-methyl-N-[1-(2-phenylethyl)-4-piperidyl]indole-3-carboxamide, melting at 159°–162° C. The crude product (3.9 g) was recovered from the mother liquor.

EXAMPLE 2

To a suspension of 2.3 g of 5-acetoxy-2-methylindole-3-carboxylic acid in 60 ml of ethyl acetate was added 2 ml of thionyl chloride and the mixture was refluxed for 4 hours on a water bath. After the solvent was concentrated and the excess thionyl chloride was removed, 80 ml of ethyl acetate was added to the residue and an insoluble material was filtered off. To the filtrate was added 2 g of 4-amino-1-(2-phenylethyl)piperidine in 2 ml of pyridine, and the mixture was stirred at room temperature for 3 hours. The precipitated material was filtered off and the filtrate was shaken with a dilute hydrochloric acid solution and the water layer was separated, neutralized with potassium carbonate and then extracted with ethyl acetate. The organic layer was washed with water, dried and then concentrated. The precipitated crystals were filtered to give crude 5-acetoxy-2-methyl-N-[1-(2-phenylethyl)-4-piperidyl]-indole-3-carboxamide. To a suspension of the crude product in 50 ml of methanol was added a solution of 1 g of potassium hydroxide in methanol. The mixture was stirred until a homogeneous solution was obtained. Then the methanol was distilled off, to the residue was added a dilute hydrochloric acid solution to once acidify and the mixture was made alkaline by an aqueous ammonia solution. The precipitated crystals were filtered and recrystallized from methanol to give 5-hydroxy-2-methyl-N-[1-(2-phenylethyl)-4-piperidyl]indole-3-carboxamide as white crystals, melting at 232°–236° C. with decomposition. The corresponding hydrochloride melts at 285°–288° C. with decomposition.

This compound also can be prepared by condensing directly 5-hydroxy-2-methylindole-3-carboxylic acid with 4-amino-1-(2-phenylethyl)piperidine in tetrahydrofuran by using dicyclohexylcarbodiimide as a dehydrating agent as follows:

A mixture of 5 g of 5-hydroxy-2-methylindole-3-carboxylic acid, 5.3 g of 4-amino-1-(2-phenylethyl)piperidine and 5.9 g of dicyclohexylcarbodiimide in 200 ml of tetrahydrofuran was refluxed under heating for 2 hours. After cooling, the precipitated crystals were filtered to give a mixture of an objective product and dicyclohexylurea. The filtrate was concentrated, and then the residue was crystallized from ethyl acetate to give the objective product.

The obtained mixture was extracted with 100 ml of hot tetrahydrofuran and the insoluble dicyclohexylurea was filtered off. The filtrate was concentrated and the residue was crystallized from ethyl acetate. The crystals were filtered and combined with the above crystalline objective product. The crystals (6.9 g) were recrystallized from methanol to give the same compound as white crystals as above mentioned, melting at 232°–236° C. with decomposition.

EXAMPLE 3

To a mixture of 3.2 g of 5-hydroxy-2-methylindole-3-carboxylic acid and 3.7 g of 4-amino-1-(3-phenylpropyl)piperidine in 60 ml of tetrahydrofuran was added 3.8 g of dicyclohexylcarbodiimide, and the whole mixture was refluxed for 2 hours. After cooling, the precipitated dicyclohexylurea was filtered off and the filtrate was concentrated. The residue was crystallized from ethyl acetate. The crystals were filtered with suction, and recrystallized from a mixture of ethyl acetate and methanol to give 5-hydroxy-2-methyl-N-[1-(3-phenylpropyl)-4-piperidyl]indole-3-carboxamide, melting at 181°–184° C. The compound was precipitated as a monohydrate at first, but the water of crystallization was evaporated by vacuum drying over 3 hours at 90° C.

EXAMPLE 4

A mixture of 4 g of 5-hydroxy-2,6-dimethylindole-3-carboxylic acid, 4 g of 4-amino-1-(2-phenylethyl)piperidine and 4 g of dicyclohexylcarbodiimide in 180 ml of tetrahydrofuran was refluxed under heating for 5 hours. After the reaction mixture was allowed to stand overnight, the precipitated crystals were filtered with suction to give a mixture of the objective product and dicyclohexylurea. The mixture was extracted with a mixture of 50 ml of 5% hydrochloric acid and 50 ml of ethanol under heating to transfer a soluble material into the solvent as an extract. This procedure was repeated three times. The collected extracts were cooled with ice and the precipitated needles were filtered. The needles were recrystallized from 50% aqueous ethanol to give 5-hydroxy-2,6-dimethyl-N-[1-(2-phenylethyl)-4-piperidyl]indole-3-carboxamide hydrochloride hemihydrate, melting at 293°–295° C. with decomposition.

EXAMPLE 5

To a solution of 0.6 g of 5-fluoro-N-(4-piperidyl)indole-3-carboxamide in a mixture of 50 ml of toluene and 10 ml of dimethylformamide were added 0.43 g of 2-phenylethylbromide and 1 g of potassium carbonate, and the whole mixture was stirred while heating and refluxing for 7 hours. After cooling, to the reaction mixture was added 50 ml of ice-cold water and stirred for 1 hour. The precipitated crystals were filtered, and washed with water and ethyl acetate. An organic layer was separated from the filtrate, dried over magnesium sufate and concentrated under reduced pressure. The residue was treated with a small amount of ethyl acetate to crystallize, and the crystals were filtered and combined with the crystals obtained as above. All of the crystals were recrystallized from methanol to give 5-fluoro-N-[1-(2-phenylethyl)-4-piperidyl]indole-3-carboxamide, melting at 238°–240° C.

The following indole-3-carboxamide derivatives can be prepared in a similar manner as above Examples:

(6) 5-Hydroxy-2-methyl-N-[1-(2-phenylethyl)-4-piperidyl]indole-3-carboxamide, melting at 214°–215° C.
(7) 6-Bromo-5-hydroxy-2-methyl-N-[1-(2-phenylethyl)-4-piperidyl]indole-3-carboxamide monohydrate, melting at 223°–224° C.
(8) 5-Hydroxy-2-methyl-N-[1-(2-(p-chlorophenyl)ethyl)-4-piperidyl]indole-3-carboxamide, melting at 240°–242° C. with decomposition
(9) 2-Methyl-N-[1-(2-phenylethyl)4-piperidyl]indole-3-carboxamide, melting at 160°–163° C.
(10) 5-Hydroxy-2-methyl-N-[1-(2-phenoxyethyl)-4-piperidyl]indole-3-carboxamide monohydrate, melting at 185°–189° C.
(11) 5-Methoxy-2-methyl-N-[1-(2-phenylethyl)-4-piperidyl]indole-3-carboxamide, melting at 214°–216° C.
(12) 2-Methyl-N-[1-(2-phenoxyethyl)4-piperidyl]indole-3-carboxamide, melting at 138°–140° C.
(13) 5-Fluoro-2-methyl-N-[1-(2-phenoxyethyl)-4-piperidyl]indole-3-carboxamide, melting at 143°–145° C.
(14) 2-Methyl-N-[1-(3-phenylpropyl)-4-piperidyl]indole-3-carboxamide, melting at 148°–150° C.
(15) 6-Bromo-5-hydroxy-2-methyl-N-[1-(3-phenylpropyl)-4-piperidyl]indole-3-carboxamide, melting at 215°–217° C.
(16) 5-Hydroxy-2,6-dimethyl-N-[1-(3-phenylpropyl)-4-piperidyl]indole-3-carboxamide, melting at 215°–216° C.
(17) 5-Hydroxy-2-methyl-N-[1-(3-phenoxypropyl)-4-piperidyl]indole-3-carboxamide hydrochloride, melting at 269°–279° C. with decomposition
(18) 5-Fluoro-2-methyl-N-[1-(2-p-methoxyphenyl)ethyl)-4-piperidyl]indole-3-carboxamide, melting at 205°–208° C.
(19) 6-Chloro-5-hydroxy-2-methyl-N-[1-(2-phenylethyl)-4-piperidyl]indole-3-carboxamide
(20) 5-Hydroxy-2-methyl-N-[1-(2-(3,4-dimethoxyphenyl)ethyl)-4-piperidyl]indole-3-carboxamide hydrochloride, melting at 284°–288° C. with decomposition
(21) 5-Hydroxy-2,N-dimethyl-N-[1-(2-phenylethyl)-4-piperidyl]indole-3-carboxamide
(22) 5-Hydroxy-2,N-dimethyl-N-[1-(2-(3,4-dimethoxyphenyl)ethyl)-4-piperidyl]indole-3-carboxamide
(23) 5-Benzyloxy-2-methyl-N-[1-(2-phenylethyl)-4-piperidyl]indole-3-carboxamide
(24) 5-Hydroxy-2-methyl-N-[1-(2-(p-methylphenyl)ethyl)-4-piperidyl]indole-3-carboxamide
(25) 5-Hydroxy-2-methyl-N-[1-(2-phenylethyl)-3-pyrrolidinyl]indole-3-carboxamide
(26) 5-Hydroxy-2-methyl-N-[1-(2-phenylethyl)-4-azepinyl]indole-3-carboxamide
(27) 5-Hydroxy-2-methyl-N-[1-(4-phenylbutyl)-4-piperidyl]indole-3-carboxamide, melting at 217°–218° C.
(28) 5-Fluoro-2-methyl-N-[1-(3-phenylpropyl)-4-piperidyl]indole-3-carboxamide, melting at 165°–166° C.
(29) 5-Hydroxy-2-methyl-N-[1-(1-methyl-3-phenylpropyl)-4-piperidyl]indole-3-carboxamide hydrochloride, melting at 264°–269° C. with decomposition
(30) 5-Hydroxy-2-methyl-N-[1-(3-(p-methoxyphenyl)-1-methylpropyl)-4-piperidyl]indole-3-carboxamide
(31) 5-Hydroxy-2-methyl-N-[1-(3-(p-hydroxyphenyl)-1-methylpropyl)-4-piperidyl]indole-3-carboxamide
(32) 5-Hydroxy-2,N-dimethyl-N-[1-(3-phenylpropyl)-4-piperidyl]indole-3-carboxamide
(33) 5-Hydroxy-2-methyl-N-[1-(3-(p-methoxyphenyl)propyl)-4-piperidyl]indole-3-carboxamide hemihydrate, melting at 178°–181° C.
(34) 5-Hydroxy-2,N-dimethyl-N-[1-(3-(p-methoxyphenyl)propyl)-4-piperidyl]indole-3-carboxamide
(35) 5-Hydroxy-2-methyl-N-[1-(3-(p-hydroxyphenyl)propyl)-4-piperidyl]indole-3-carboxamide, melting at 222°–226° C. with decomposition
(36) 5-Hydroxy-2-methyl-N-[1-(2-phenylthioethyl)-4-piperidyl]indole-3-carboxamide
(37) 5-Hydroxy-2,N-dimethyl-N-[1-(3-(p-hydroxyphenyl)-1-methylpropyl)-4-piperidyl]indole-3-carboxamide
(38) 5-Methoxy-2-methyl-N-[1-(3-phenylpropyl)-4-piperidyl]indole-3-carboxamide, melting at 176°–178° C.

Although the present invention has been adequately discussed in the foregoing specification and examples included therein, one readily recognizes that various changes and modifications may be made without departing from the spirit and scope thereof.

What is claimed is:
1. A 3-indolecarboxamide compound of the formula

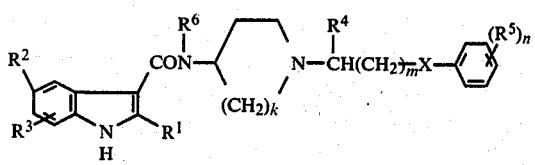

inclusive of compounds selected from the group consisting of pharmaceutically acceptable acid addition salt forms thereof, hydrate forms thereof and mixtures thereof, wherein $R^1$ is a hydrogen atom or $C_{1-4}$ alkyl group; each of $R^2$ and $R^3$ is a hydrogen atom, a halogen atom, a $C_{1-4}$ alkyl group, a $C_{1-4}$ alkoxy group, a benzyloxy group, a $C_{2-6}$ alkanolyloxy group or a hydroxyl group; $R^4$ is a hydrogen atom or a $C_{1-4}$ alkyl group; $R^5$ is a hydrogen atom, a halogen atom, a $C_{1-4}$ alkyl group, a $C_{1-4}$ alkoxy group or a hydroxyl group; $R^6$ is a hydrogen atom or a $C_{1-4}$ alkyl group; X is an oxygen atom, a sulfur atom or a direct bond; each of k and m is an integer of 1 to 3; and n is 1 or 2.

2. The compound of claim 1, wherein $R^1$ is a hydrogen atom or a $C_{1-4}$ alkyl group; $R^2$ is a hydrogen atom, a halogen atom, a $C_{1-4}$ alkoxy group or a hydroxyl group; $R^3$ is a hydrogen atom, a halogen atom or a $C_{1-4}$ alkyl group; $R^4$ is a hydrogen atom or a $C_{1-4}$ alkyl group; $R^5$ is a hydrogen atom, a halogen atom, a $C_{1-4}$ alkoxy group or a hydroxyl group on the 4-position of the benzene ring; $R^6$ is a hydrogen atom; X is a direct bond; k is 2; m is 1 or 2; and n is 1.

3. The compound of claim 1 wherein $R^1$ is a hydrogen atom or a $C_{1-4}$ alkyl group; $R^2$ is a hydroxyl group; $R^3$ is a hydrogen atom, a halogen atom or a $C_{1-4}$ alkyl group; $R^4$ is a hydrogen atom or a $C_{1-4}$ alkyl group; $R^5$ is a hydrogen atom, a halogen atom, a $C_{1-4}$ alkoxy group or a hydroxyl group on the 4-position of the benzene ring; $R^6$ is a hydrogen atom; X is a direct bond; k is 2; m is 1 or 2; and n is 1.

4. The compound of claim 1: 5-Fluoro-2-methyl-N-[1-(2-phenylethyl)-4-piperidyl]indole-3-carboxamide.

5. The compound of claim 1: 5-Hydroxy-2-methyl-N-[1-(2-phenylethyl)-4-piperidyl]indole-3-carboxamide.

6. The compound of claim 1: 5-Hydroxy-2-methyl-N-[1-(2-phenylethyl)-4-piperidyl]indole-3-carboxamide hydrochloride.

7. The compound of claim 1: 5-Hydroxy-2-methyl-N-[1-(3-phenylpropyl)-4-piperidyl]indole-3-carboxamide.

8. The compound of claim 1: 5-Hydroxy-2,6-dimethyl-N-[1-(2-phenylethyl)-4-piperidyl]indole-3-carboxamide.

9. The compound of claim 1: 6-Bromo-5-hydroxy-2-methyl-N-[1-(2-phenylethyl)-4-piperidyl]indole-3-carboxamide.

10. The compound of claim 1: 5-Methoxy-2-methyl-N-[1-(2-phenylethyl)-4-piperidyl]indole-3-carboxamide.

11. A pharmaceutical composition for the prevention and treatment of circulatory diseases containing an amount effective to prevent or treat circulatory diseases of the compound of claim 1 and a pharmaceutically acceptable carrier thereof.

12. The pharmaceutical composition of claim 11 wherein said effective amount ranges from 0.01 to 10 mg/kg.

* * * * *